United States Patent [19]
Can

[11] Patent Number: 5,515,157
[45] Date of Patent: *May 7, 1996

[54] GEM VIEWING AND MANIPULATION APPARATUS

[76] Inventor: Hanna Can, 15036 Tyacke Dr., Burnsville, Minn. 55337

[ * ] Notice: The term of this patent shall not extend beyond the expiration date of Pat. No. 5,422,711.

[21] Appl. No.: 460,254

[22] Filed: Jun. 2, 1995

Related U.S. Application Data

[63] Continuation-in-part of Ser. No. 138,355, Oct. 18, 1993, Pat. No. 5,422,711.

[51] Int. Cl.$^6$ ................................................. G01N 21/87
[52] U.S. Cl. ............................................................ 356/30
[58] Field of Search ............................................ 356/30

[56] References Cited

U.S. PATENT DOCUMENTS

| | | | |
|---|---|---|---|
| 1,700,496 | 1/1929 | Heitzler | 356/30 |
| 1,700,497 | 1/1929 | Heitzler | 356/30 |
| 2,494,078 | 4/1948 | Woodruff | 356/30 |
| 2,742,813 | 4/1956 | Zeininger | 356/30 |
| 5,138,486 | 8/1992 | Meyer et al. | 359/363 |
| 5,422,711 | 6/1995 | Can | 356/30 |

FOREIGN PATENT DOCUMENTS

| | | | |
|---|---|---|---|
| 3914882 | 11/1990 | Germany | 356/30 |
| 56-120939 | 9/1981 | Japan | 356/30 |
| 58-200210 | 11/1983 | Japan | 356/30 |

*Primary Examiner*—F. L. Evans
*Attorney, Agent, or Firm*—Palmatier, Sjoquist & Helget

[57] ABSTRACT

The present invention provides an improved apparatus for viewing gems that provides a magnified image simultaneously viewable by several individuals, and which allows a customer to manipulate the gem while restricting the customer's access to the gem and without any physical contact with the gem by the customer. The apparatus is comprised of a video image generator including a magnifying lens unit provides a viewing region for placement of a gem. A gem holder comprised of a pair of opposing grasping members pivotally and slidably mounted on a post extending from support structure. The opposing members are configured to grasp a gem, manipulate and reposition the gem in the viewing region as desired for viewing of the gem. A television monitor displays the magnified image of the gem. The device is particularly applicable in the retail sales of jewelry.

5 Claims, 2 Drawing Sheets

GEM VIEWING AND MANIPULATION APPARATUS

This is a continuation-in-part of co-pending application Ser. No. 08/138,355 filed Oct. 18, 1993, issued Jun. 6, 1995 as U.S. Pat. No. 5,422,711.

BACKGROUND OF THE INVENTION

This invention relates to an apparatus for viewing objects, more specifically, it relates to apparatus to allow the viewing of the magnified image of gems on a television monitor while simultaneously manipulating the gems.

The equipment conventionally used for magnifying and viewing gems are the eyepiece, commonly known as the loupe, and the microscope. Both the loupe and microscope can be difficult to use, especially for lay people, and are cumbersome for use during sales presentations. A principal disadvantage is that only one person can view the image of the gem through either of these apparatus at any one time. This is particularly disadvantageous when a jeweler or gemologist is attempting to point out specific features or flaws in a particular gem. An additional disadvantage is that the loupe requires the viewer to hold or come into close contact with the gem being viewed. Additionally, with conventional viewing equipment the jeweler or gemologist may loose visual contact with the gem during handling by the customer, presenting security problems.

SUMMARY OF THE INVENTION

The present invention provides an improved apparatus for viewing gems that provides a magnified image simultaneously viewable by several individuals, and which allows a customer to manipulate the gem while restricting the customer's access to the gem and without any physical contact with the gem by the customer. The apparatus is comprised of a video image generator including a magnifying lens unit provides a viewing region for placement of a gem. A gem holder comprised of a pair of opposing grasping members pivotally and slidably mounted on a post extending from the support structure. The opposing members are configured to grasp a gem, manipulate and reposition the gem in the viewing region as desired for viewing of the gem. A television monitor displays the magnified image of the gem. The device is particularly applicable in the retail sales of jewelry.

A feature of the present invention is that it permits several individuals to simultaneously view the same image of a gem. This allows specific features of the gem to be pointed out by referencing the features on the image shown on the television monitor.

An additional advantage of the invention is that the actual gem and the magnified image of the gem can both be viewed simultaneously.

Another advantage and feature of the invention is that physical access by customers to gems placed on the receiving tray or in the opposing members is restricted, while still allowing the customer to view the magnified image of a gem and to manipulate the gem.

A significant feature of the invention is that it allows an individual, such as a customer, to view a magnified image of a gem while manipulating the gem, and eliminates or minimizes the need for the physical handling of the gem. This provides security and helps to keep the gem clean.

Another advantage of the present invention is that by focusing through the gem imperfections or flaws may be more easily identified and viewed, especially by lay people.

Another feature of the present invention is that a convenient side by side magnified viewing of two or more gems may be performed permitting direct comparisons between gems. Additionally, gems may be viewed with color comparison charts.

An additional feature of the invention is that a magnified video image of the gem may be conveniently recorded by way of conventional video recording apparatus.

DETAILED DESCRIPTION OF THE PREFERRED EMBODIMENTS

The apparatus as depicted is intended principally for use by those in the jewelry business, especially the retail sale of jewelry although other uses will become apparent. "Gems" as used herein is intended to encompass all stones, jewelry, watches, or other items which may be viewed in the apparatus.

Figure 1:
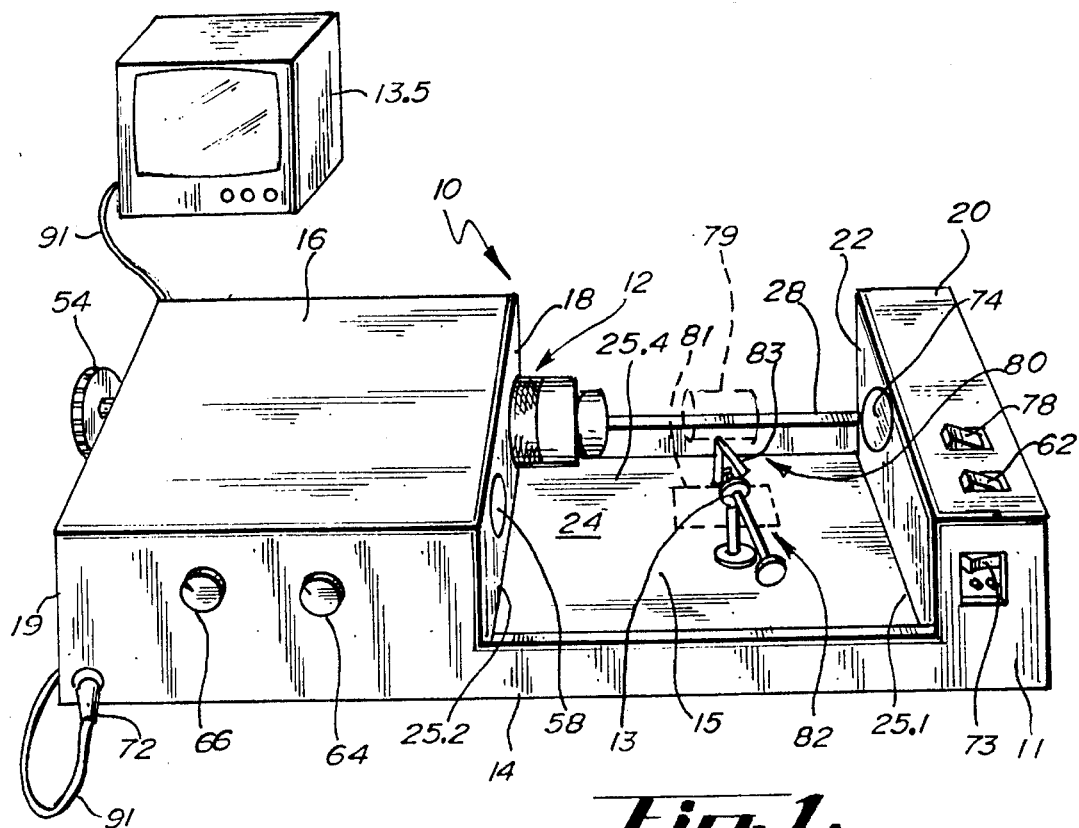
FIG. 1 is a perspective of the invention.
Figure 2:
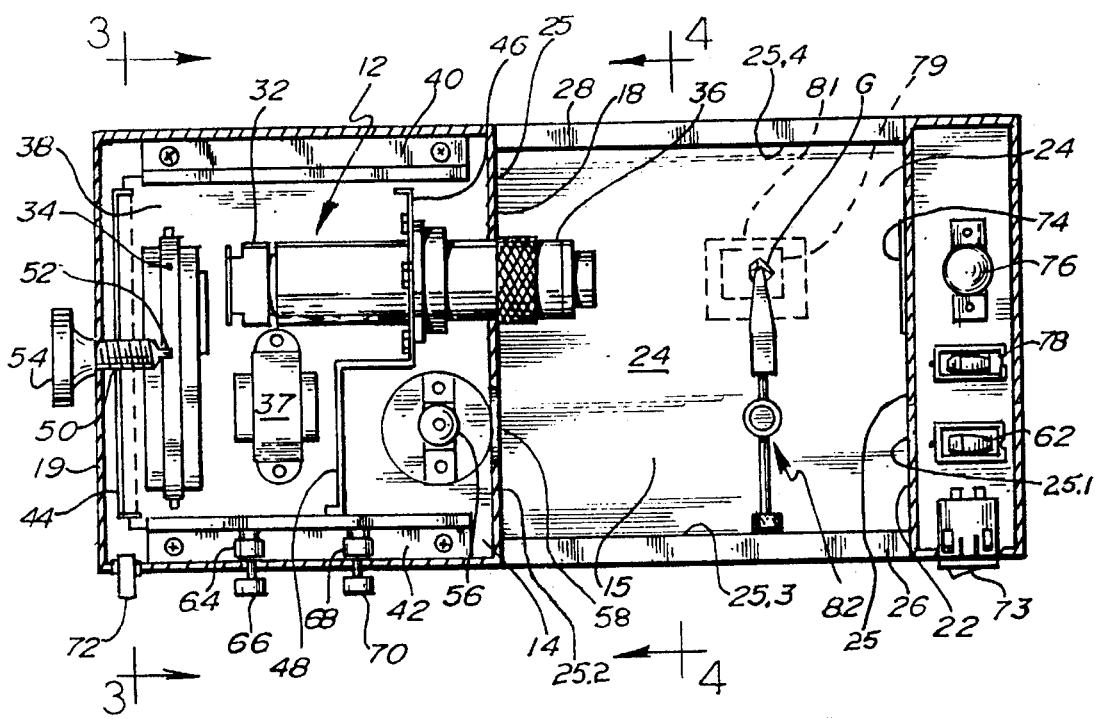
FIG. 2 shows a plan view with the first enclosure and second enclosure removed, showing the general layout of the components.

Referring to FIGS. 1 and 2, the viewing and manipulation apparatus is shown and is indicated by the numeral 10, with a gem indicated by letter G. FIG. 1 shows the apparatus with enclosures in place. In FIG. 2 portions of the enclosures are removed to show the general layout of components. Internal wiring is not shown. The apparatus 10 is principally comprised of a support structure 11, an electronic video image generator 12, a moveable gem holder 13, a video image display 13.5. The support structure 11 includes a horizontal base 14 having an upper surface 15, a first enclosure 16 including a first upright panel 18 and a back panel 19, and a second enclosure 20 with a second upright panel 22 opposite the first upright panel 18. Intermediate the two upright panels 18, 22 on the horizontal base 14 is a receiving region 24. The receiving region 24 has an outer perimeter 25, a first end 25.1; a second end 25.2, a first side 25.3, and a second side 25.4. Two raised edges 26, 28 extend between the two upright panels 18, 22 along the first side 25.3 and the second side 25.4 respectively. Included within the first enclosure 16 is the video image generator 12 which comprises the components of a television video camera and principally includes a solid state sensor 32, a circuit board 34, and a magnifying lens unit 36 extending out the first upright panel 18. The lens unit 36 is directed horizontally toward the second upright panel 22. A transformer 37 provides power for the image generator 12. The lens unit 36, the sensor 32, the circuit board 34, and the transformer 37 are all mounted by screws, rivets or other suitable means to a sliding chassis 38 which is also part of the support structure 11. The sliding chassis 38 is supported by and rides in guides 40, 42 which are attached to the base 14. The sliding chassis 38 is formed of a rigid material such as sheet metal. The guides 40, 42 may be suitably formed of machined aluminum or plastic.

Figure 4:
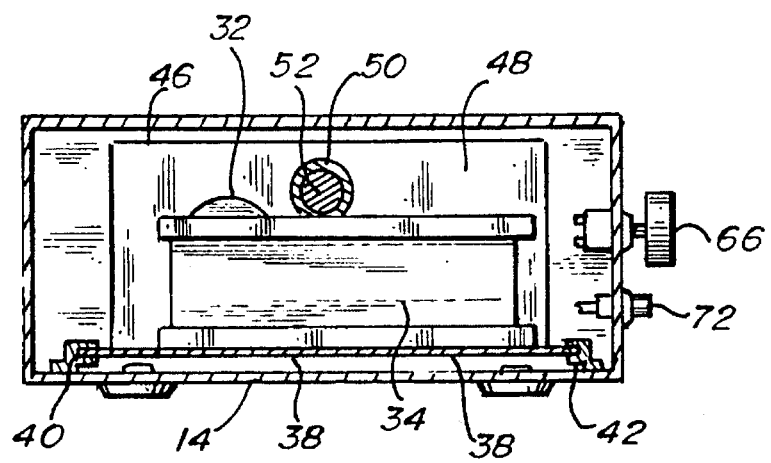
FIG. 4 is a sectional taken at line 4—4 of FIG. 2.

Referring to FIGS. 2 and 4, the sliding chassis 38 has a first vertical wall 44, a second vertical wall 46, and a third vertical wall 48. The lens unit 36 and solid state sensor 32 are mounted on the second vertical wall 46. Suitably attached to the first vertical wall 44 is drive nut 50. A threaded shaft 52 is engaged within the drive nut 50 and extends through and is rotatably mounted to the back panel 19. A knob 54 is attached to the shaft. Rotation of the knob 54 adjustably slides the chassis 38 forwardly and rearwardly with respect to the back panel 22.

Located behind the first panel 18 is a first light source 56 which may provide illumination of the gem at an oblique angle relative to the camera through an aperture 58 which is best shown in FIG. 4. A lens or diffuser 60 is attached to the first upright panel 18 and covers the aperture 58. A rocker switch 62 mounted on the second enclosure controls the first light source 56. The first light source 56 may also be adjustable relative to its intensity by conventional means. Also extending out of the first enclosure is a color control 64 with a knob 66, an iris control 68 with a knob 70, and a video output jack 72. A combination power switch and power cord receptacle 73 is shown connected to the second enclosure 20.

Figure 3:
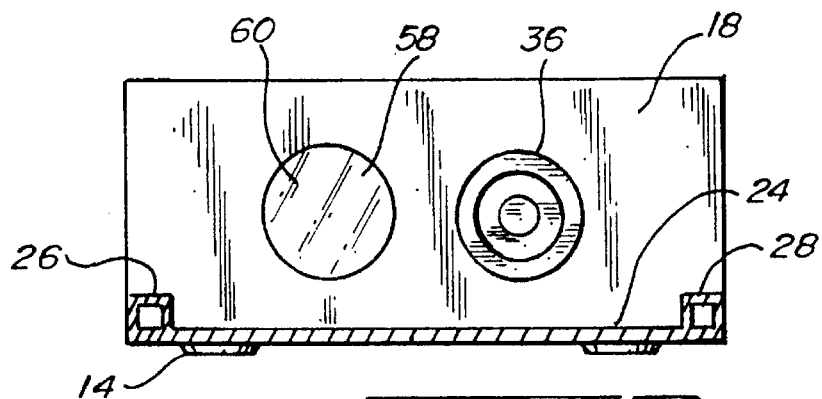
FIG. 3 is a sectional taken at line 3—3 of FIG. 2 and shows the sliding chassis.

The adjustable iris 71 is contained within the magnifying lens unit 36 and is shown in FIG. 3.

As best seen in FIG. 1, attached to the second upright panel 22 is a background screen 74 which provides the background when viewing the gem G. The screen 74 may be back lit by way of a second light source 76 within the second enclosure 20, best shown in FIG. 2. The background screen 74 may be interchangeable with alternate screens having different colors, shades and/or different degrees of translucency. A rocker switch 78 controls the second light source 76. The second light source 76 also may be adjustable by conventional means with regard to its intensity.

The video image generator 12 may be a conventional video camera with the components of the camera mounted on the sliding chassis 38 and contained within the first enclosure 16. A suitable video camera would be a model VCM7250 by Philips Consumer Electronics B.V. An appropriate magnifying lens unit would be a microscope lens with a variable zoom of 0.75× to 3× power and a working distance of 61 mm. The working distance of the lens unit 36 defines a viewing region 79 indicated by phantom lines above the base 14 and intermediate the first and second upright panels 18, 22. The gem is positioned and manipulated within the viewing region 79. Immediately below the viewing region 79 is the placement zone 81 positioned on the base 14.

Figure 5:
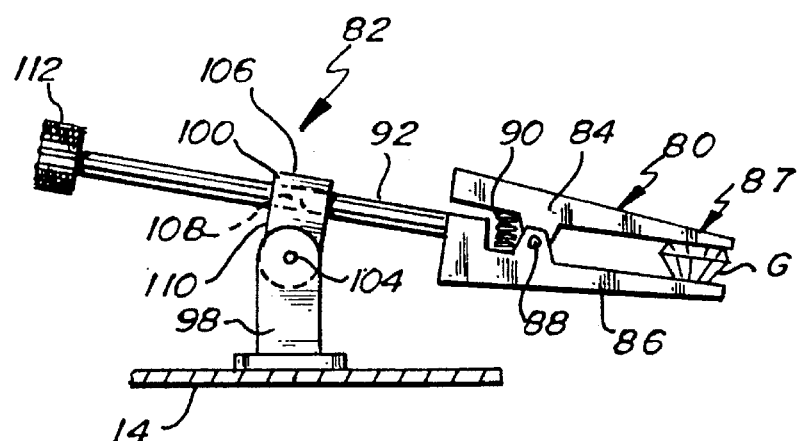
FIG. 5 is a detail figure of the grasping means and manipulation means of the invention.

The moveable gem holder 13 is comprised of a grasping means 80 and a manipulation means 82 shown in FIGS. 1, 2 and 5. Referring to FIG. 5, the grasping means 80 is comprised of a clip 83 formed of a pair of opposing members 84, 86 having a grasping portion 87 and pivotally connected at a pin 88, a spring 90 is inserted between the opposing members 84, 86 to provide an inward bias.

The manipulation means 82 is comprised principally of a moveable manipulation member configured as a rod 92, a post 98, a post extension 100, a pin 104, an upper portion 106, a hole 108, and a lower portion 110. The post 98 is suitably attached to the base 14 by way of a screws, adhesives, or other appropriate means. The post extension 100 is pivotally attached to the post 98 at a first moveable joint 111 by a pin 104. The post extension 100 has an upper portion 106 which includes a hole 108 and a lower portion 110 to which the upper portion 106 is rotatably attached by suitable means. The rod 92 is connected to one of the opposing members 84, 86 and extends through a pivoting post hole 108 at a second moveable joint 113 in the post extension 100. A knurled knob 112 is attached to the end of the rod 92 to comprise a manual manipulation member. The hole 108 is sized to allow the rod 92 to be rotatably and slidably adjusted therein.

The sizing and configuration of the component parts of the grasping means 80 and manipulation means 82 allows the grasping of gems placed on the receiving region 24 immediately below the viewing region 79 in an area shown as the placement zone 81. Gems grasped by the grasping means 80 in the placement zone 81 may be elevated into and manipulated within the viewing region 79. Alternate manipulation means may also be utilized such as a flexible rod which retains a deformation. In such a case the flexible rod constitutes a moveable joint. The function of the manipulation means is to be able to adjust the position of the gem and have the gem G be retained in the adjusted position.

Alternate grasping means would include an adhesive or suction elements to grasp the gem G. The function of the grasping means is to clamp or attach to the gem while leaving substantially all of the gem G exposed for viewing. Additionally, more than one grasping means and manipulation means can be utilized with said means mounted above, adjacent to, or opposite the placement of the grasping means 80 and manipulation means 82 as shown. This would allow comparative viewing of multiple gems and also may be utilized for viewing a gem in conjunction with a reference chart such as for color comparison.

Connection means connect the video image generator 12 to the image display 13.5.

The connection means may be conventional such as a coaxial cable or fiber optic cable. Additionally, the connection means may be wireless utilizing infrared, ultrasonic, or radio frequency transmitters and receivers. The video image display may be a conventional television monitor or other display devices such as liquid crystal screens or other flat panel screens.

The apparatus is utilized as follows: Referring to FIGS. 1 and 2, a video image display is connected to the apparatus by connection means. The rocker switches 62, 78 are turned on as desired to control the first light source 56 and the second light source 76. A gem G is placed within the opposing members 84, 86 or is placed in the placement zone 81 and is then grasped by the opposing grasping members 84, 86. The gem G engaged by the opposing grasping members 84, 86 is manipulated by utilizing the pivoting, sliding, and rotational characteristics of the rod 92, the post 98, and the post extension 100, and is positioned within the viewing range as desired. Appropriate magnification of the lens is selected and the lens 36 is focused by rotation of knob 54 which minutely slides the sliding chassis 38 containing the camera lens 36 and other camera components. The color control 64 and iris control 68 may be adjusted by way of knobs 66, 70. With an expanded iris 71 a shorter depth of field is given and the focus may be taken directly through the gem by adjusting the focus knob 54 to focus on and identify flaws and imperfections in the gem. A restricted iris gives a longer field of view and permits the gem to be rotated or otherwise repositioned in the viewing region 79 while still maintaining the gem in focus.

When utilized in jewelry sales presentations, the customer can adjust the focus by way of the knob 54 and can manipulate the gem G being viewed without any actual touching of the gem G by the customer. The arrangement of the first enclosure 16, the second enclosure 20, and the grasping means and manipulation means effectively discourages and restricts access to the viewing region 79 and the placement zone 81 and gems placed therein by customers. Any reaching into the viewing region 79 or the placement zone 81 by the customer is awkward and obvious. While the gem G is being manipulated the jeweler can easily point out specific features on the image shown on the television monitor.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention. For example, the apparatus may be arranged in a generally upright configuration with the video image generator, the lens unit, and the viewing region substantially vertically aligned with the viewing region either above or below the video image generator.

What is claimed:

1. A viewing and manipulation apparatus for gems, the apparatus comprising:

a) a support structure with a horizontal base;

b) an electronic video image generator comprised of a image sensor device and a magnifying lens unit, the image generator supported by the support structure and having a viewing region adjacent the lens unit;

c) a gem holder comprised of a grasping means for grasping a gem and a manipulation means, the gem holder connected to the support structure and extending to the viewing region;

d) an image display unit with connection means connecting the unit to the image generator; and e) a light source mounted to the base, the light source positioned to direct light at an oblique angle toward the viewing region with respect to the image generator.

2. The viewing and manipulation apparatus of claim 1, wherein the grasping means comprises a plurality of grasping members to grasp the gem.

3. The viewing and manipulation apparatus of claim 1, wherein the manipulation means comprises a pivoting joint to allow the gem to be rotated within the viewing region.

4. The viewing and manipulation apparatus of claim 1, wherein the electronic image generator has a depth of field that is adjustable, whereby internal flaws in gems may be focused upon, and whereby entire gems may be focused upon.

5. A viewing and manipulation apparatus for gems, the apparatus comprising:

a) a support structure;

b) a video image generator comprised of an image sensor and a lens unit, the image generator attached to the support structure, the image generator having a viewing region in front of the lens unit for positioning a gem for viewing;

c) a gem holder comprised of a grasping member to hold the gem, a manipulation member connected to the grasping member for manipulating the gem, and a moveable joint, the grasping member connected to the support structure through the moveable joint whereby the gem may be moved about and repositioned within the viewing region by way of the manipulation member;

e) a video image display connected to the image generator for producing an enlarged video image of the gem; and e) a light source mounted to the support structure, the light source positioned to direct light at an oblique angle toward the viewing region with respect to the image generator.

* * * * *